United States Patent
Kim et al.

(10) Patent No.: US 11,401,343 B2
(45) Date of Patent: Aug. 2, 2022

(54) ANTI-MSLN ANTIBODY AND PHARMACEUTICAL COMPOSITION FOR CANCER TREATMENT COMPRISING SAME

(71) Applicants: GREEN CROSS CORPORATION, Yongin-si (KR); MOGAM INSTITUTE FOR BIOMEDICAL RESEARCH, Yongin-si (KR)

(72) Inventors: Ki Su Kim, Yongin-si (KR); Jung Hong Jeong, Yongin-si (KR); Dong Sik Kim, Yongin-si (KR); Yang Mi Lim, Yongin-si (KR); Yong Yea Park, Yongin-si (KR); Hyung Kwon Lim, Yongin-si (KR); Jong Wha Won, Yongin-si (KR)

(73) Assignees: GREEN CROSS CORPORATION, Yongin-si (KR); MOGAM INSTITUTE FOR BIOMEDICAL RESEARCH, Yongin-si (KR)

(*) Notice: Subject to any disclaimer, the term of this patent is extended or adjusted under 35 U.S.C. 154(b) by 131 days.

(21) Appl. No.: 16/651,908

(22) PCT Filed: Oct. 22, 2018

(86) PCT No.: PCT/KR2018/012493
§ 371 (c)(1),
(2) Date: Mar. 27, 2020

(87) PCT Pub. No.: WO2019/078698
PCT Pub. Date: Apr. 25, 2019

(65) Prior Publication Data
US 2020/0262928 A1    Aug. 20, 2020

(30) Foreign Application Priority Data
Oct. 20, 2017  (KR) ........................ 10-2017-0136565

(51) Int. Cl.
*C07K 16/30* (2006.01)
*A61K 38/00* (2006.01)
*C12N 15/85* (2006.01)

(52) U.S. Cl.
CPC .......... *C07K 16/3076* (2013.01); *C12N 15/85* (2013.01); *A61K 38/00* (2013.01); *C07K 2317/24* (2013.01); *C07K 2317/56* (2013.01)

(58) Field of Classification Search
CPC ............ C07K 16/3076; C07K 2317/24; C07K 2317/56; C12N 15/85; A61K 38/00
See application file for complete search history.

(56) References Cited

U.S. PATENT DOCUMENTS

| | | |
|---|---|---|
| 2011/0262448 A1 | 10/2011 | Terrett et al. |
| 2015/0322160 A1 | 11/2015 | Kahnert et al. |
| 2018/0244796 A1 | 8/2018 | Wang et al. |
| 2018/0346588 A1 | 12/2018 | Kim et al. |

FOREIGN PATENT DOCUMENTS

| | | |
|---|---|---|
| JP | 4-502408 A | 5/1992 |
| KR | 10-1554848 B1 | 9/2015 |
| KR | 10-1681795 B1 | 12/2016 |
| KR | 10-2017-36503 A | 4/2017 |
| WO | 90/07861 A1 | 7/1990 |
| WO | 2017/032293 A1 | 3/2017 |

OTHER PUBLICATIONS

Hassan et al, Journal of Clinical Oncology (2016), 34:4171-4179. (Year: 2016).*
Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Liners et al (Gly, 15(9):849-860, 2005).*
Raffit Hassan et al., "Preclinical evaluation of MORAb-009, a chimeric antibody targeting tumor-associated mesothelin", Cancer Immunity, Dec. 19, 2007, vol. 7, pp. 1-10.
Yi-Fan Zhang et al., "New High Affinity Monoclonal Antibodies Recognize Non-Overlapping Epitopes on Mesothelin for Monitoring and Treating Mesothelioma", Scientific Reports, May 21, 2015, vol. 5, No. 09928, pp. 1-14.
International Search Report for PCT/KR2018/012493 dated, May 20, 2019 (PCT/ISA/210).
Noreen R. Gonzales et al., "Minimizing the Immunogenicity of Antibodies for Clinical Application", Tumor Biology, 2005, vol. 26, No. 1, pp. 31-43 (13 pages).
Yoon et al., "A Novel T Cell-Engaging Bispecific Antibody for Treating Mesothelin-Positive Solid Tumors", Biomolecules 2020, 10, 399, published Mar. 4, 2020; doi:10.3390/biom!0030399.

* cited by examiner

*Primary Examiner* — Brad Duffy
*Assistant Examiner* — Cheom-Gil Cheong
(74) *Attorney, Agent, or Firm* — Sughrue Mion, PLLC

(57) ABSTRACT

The present invention relates to an anti-MSLN antibody and a pharmaceutical composition for cancer treatment comprising same. The anti-MSLN antibody according to the present invention has high affinity and specificity for MSLN and thus can be effectively used in cancer prevention or treatment.

13 Claims, 8 Drawing Sheets

Specification includes a Sequence Listing.

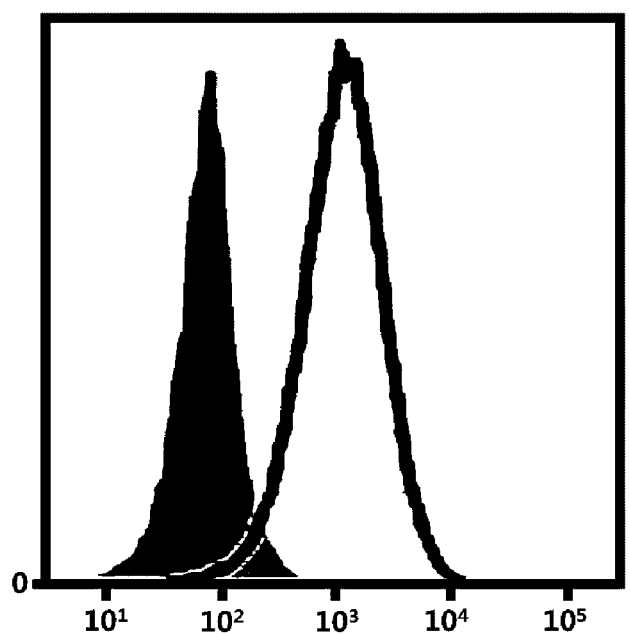
[Fig. 1]

[Fig. 2]
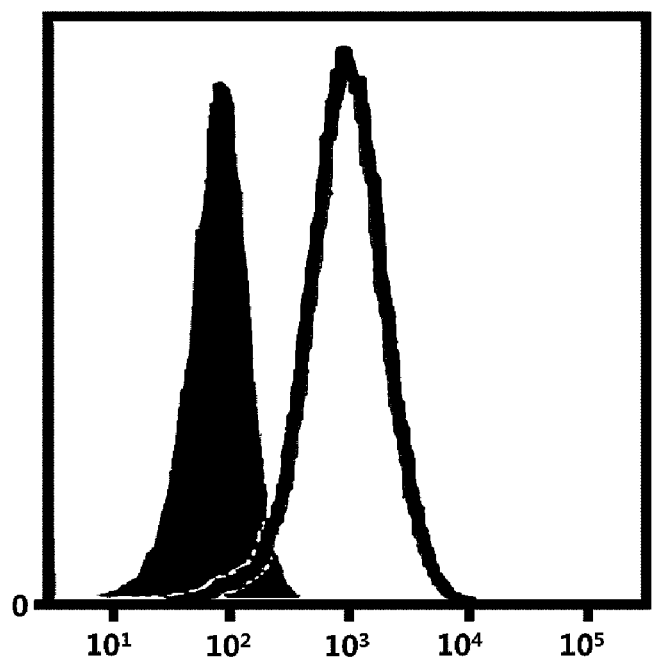

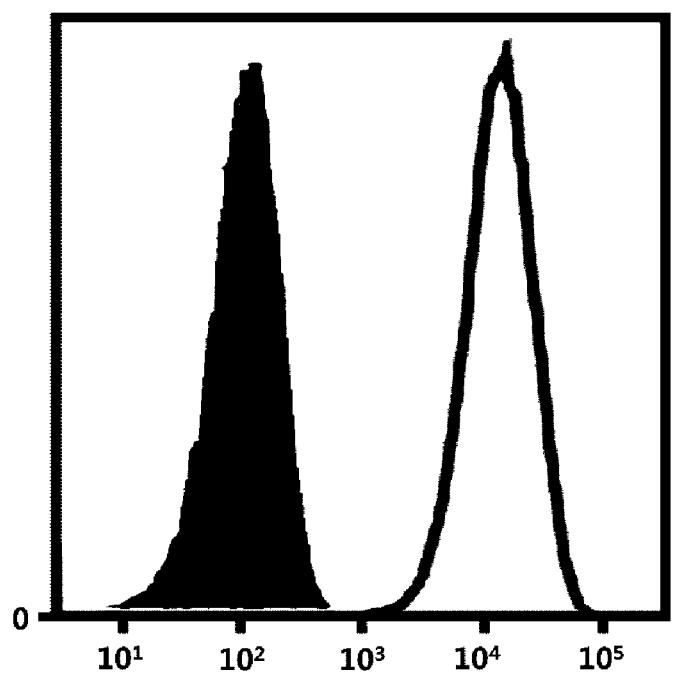
[Fig. 3]

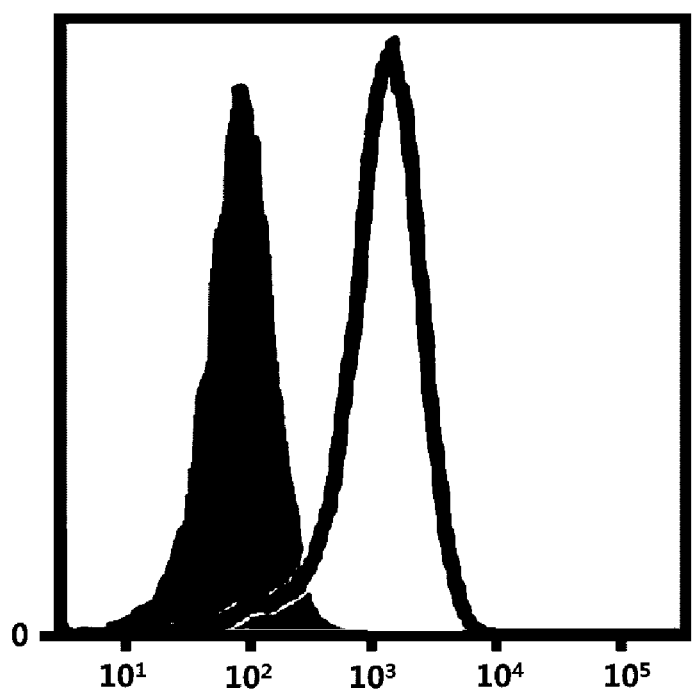

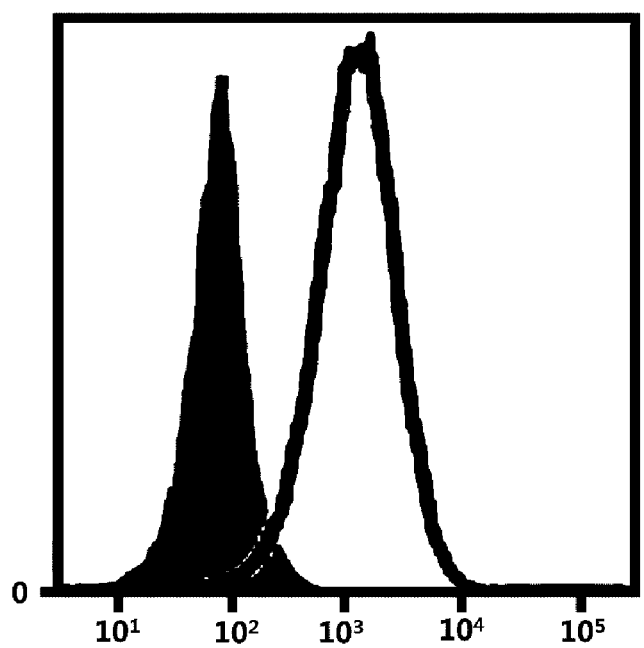
[Fig. 5]
| | Cells | Antibody | MFI |
|---|---|---|---|
| | AsPC1 | HMI323VL-1/HMI323VH-3 | 1506 |
| | AsPC1 | hIgG | 85.9 |

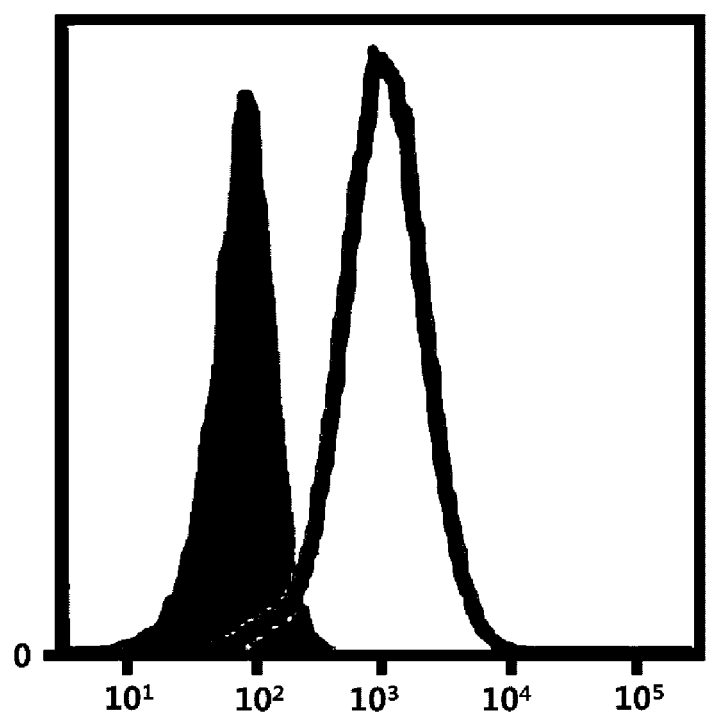

[Fig. 7]
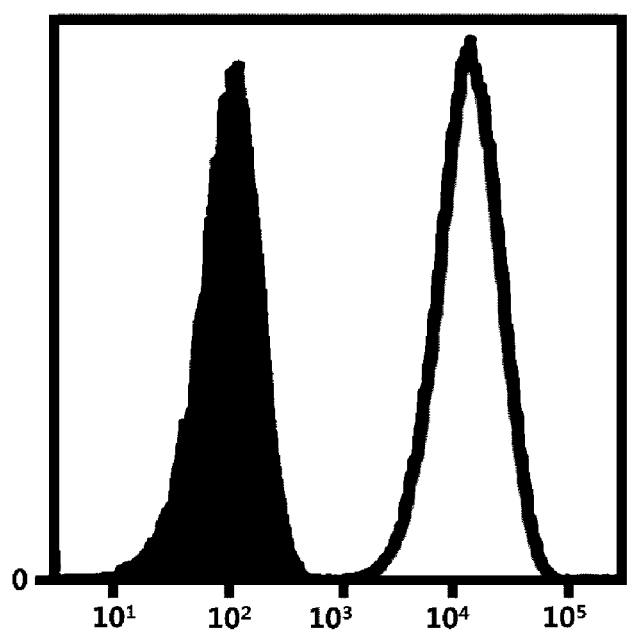

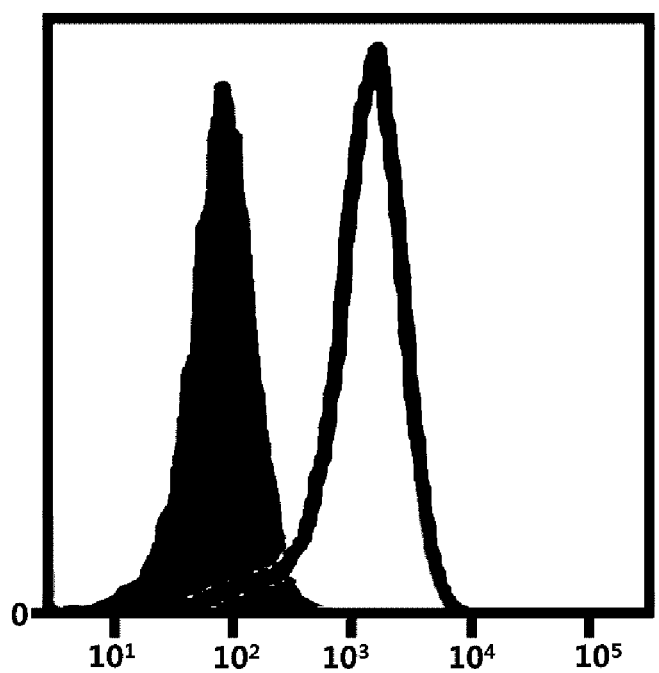
[Fig. 8]

ANTI-MSLN ANTIBODY AND PHARMACEUTICAL COMPOSITION FOR CANCER TREATMENT COMPRISING SAME

CROSS REFERENCE TO RELATED APPLICATIONS

This application is a National Stage of International Application No. PCT/KR2018/012493 filed Oct. 22, 2017, claiming priority based on Korean Patent Application No. 10-2017-0136565, filed Oct. 20, 2017.

TECHNICAL FIELD

The present invention relates to an anti-MSLN antibody and a pharmaceutical composition for treating cancer comprising the same.

BACKGROUND ART

Among various causes of death, death from cancer occurs frequently, accounting for the second-largest proportion. Various attempts have been made to treat cancer in the past. Currently, regarding treatment methods for treating cancer, administration of an anticancer agent, irradiation, or surgical operation has been carried out. However, such treatment methods may be effective in the early stages of cancer, and have a poor therapeutic effect in a terminal cancer, when cancer has spread to other tissues, or when cancer has recurred.

Recently, in order to treat cancer without side effects, studies on targeted anticancer agents using antibodies have been actively conducted. Typically, Herceptin, an anti-HER2 antibody, is used to treat breast cancer, and Avastin, an anti-vascular endothelial growth factor (VEGF) antibody, is used to treat colorectal cancer. The key to developing targeted anticancer agents using antibodies is to develop antibodies against membrane surface proteins that are overexpressed in cancer cells.

Meanwhile, mesothelin (MSLN) is a precursor polypeptide of 69 kDa to 71 kDa, and is a glycoprotein present on the cell surface of the mesothelial layer of peritoneal, pleural and pericardial cavities. To date, although the function of MSLN is not clearly elucidated, it has been reported that overexpression of MSLN is observed in mesothelioma, ovarian cancer, pancreatic cancer, gastric cancer, lung cancer, and endometrial cancer, which are cancer cells or tumor cells. In addition, studies have shown that mouse/human chimeric anti-MSLN antibodies inhibit cancer cell growth in a case where cancer cells, in which MSLN is overexpressed, are treated with such antibodies (Hassan R et al., Cancer Immun., 19; 7:20, 2007).

Accordingly, mouse antibodies that specifically bind to MSLN have been developed. However, clinical trials have not been successful due to lack of cross-reactivity between heterologous subjects. In addition, antibodies produced in patients treated with mouse-derived antibodies or chimeric antibodies have problems of causing excessive toxicity or decreasing therapeutic efficacy.

Therefore, there is a need for development of an anti-MSLN antibody that can exhibit cross-reactivity with a human while having high affinity to MSLN.

Technical Problem

The present invention is made to solve the above-mentioned problems of the prior art. An object of the present invention is to provide an antibody having high binding affinity to mesothelin (MSLN) and a pharmaceutical composition having excellent cancer treatment efficacy using the same.

However, the problem to be solved by the present invention is not limited to the above-mentioned problems, and other problems which are not mentioned will be clearly understood by those skilled in the art from the following description.

Solution to Problem

In an aspect of the present invention, there is provided an antibody, comprising a light chain variable domain (VL domain) consisting of a sequence having at least 80% identity to an amino acid sequence of SEQ ID NO: 1 and a heavy chain variable domain (VH domain) consisting of a sequence having at least 80% identity to an amino acid sequence of any one of SEQ ID NOs: 3 to 5.

In another aspect of the present invention, there is provided a polynucleotide that encodes the light chain variable domain (VL domain) and the heavy chain variable domain (VH domain) of the antibody.

In yet another aspect of the present invention, there is provided an expression vector comprising the polynucleotide.

In still yet another aspect of the present invention, there is provided a host cell transformed with the expression vector.

In still yet another aspect of the present invention, there is provided a method for producing an antibody that specifically binds to MSLN comprising a step of culturing the host cell.

In still yet another aspect of the present invention, there is provided a pharmaceutical composition for preventing or treating cancer comprising the antibody or a fragment thereof.

Advantageous Effects of Invention

Owing to high affinity and specificity to MSLN, an anti-MSLN antibody of the present invention can be effectively used for prevention or treatment of cancer.

It is to be understood that the effect of the present invention is not limited to the above-described effects, and includes all effects that are deducible from the configuration of the invention described in the detailed description or the claims of the present invention.

BRIEF DESCRIPTION OF DRAWINGS

FIG. 1 illustrates results obtained by analyzing affinity of mouse/human chimeric MI323 IgG1 to human pancreatic cancer cells (AsPC1) expressing MSLN.

FIG. 2 illustrates results obtained by analyzing affinity of mouse/human chimeric MI323 IgG1 to human pancreatic cancer cells (Capan2) expressing MSLN.

FIG. 3 illustrates results obtained by analyzing affinity of mouse/human chimeric MI323 IgG1 to human pleural mesothelioma (H226) expressing MSLN.

FIG. 4 illustrates results obtained by analyzing affinity of mouse/human chimeric MI323 IgG1 to human pancreatic cancer cells (PL45) expressing MSLN.

FIG. 5 illustrates results obtained by analyzing affinity of humanized MI323 IgG1 to human pancreatic cancer cells (AsPC1) expressing MSLN.

FIG. 6 illustrates results obtained by analyzing affinity of humanized MI323 IgG1 to human pancreatic cancer cells (Capan2) expressing MSLN.

FIG. 7 illustrates results obtained by analyzing affinity of humanized MI323 IgG1 for human pleural mesothelioma (H226) expressing MSLN.

FIG. 8 illustrates results obtained by analyzing affinity of humanized MI323 IgG1 for human pancreatic cancer cells (PL45) expressing MSLN.

DETAILED DESCRIPTION OF INVENTION

Hereinafter, the present invention will be described in detail.

In an aspect of the present invention, there is provided an antibody comprising a light chain variable domain (VL domain) consisting of a sequence having at least 80% identity to an amino acid sequence of SEQ ID NO: 1 and a heavy chain variable domain (VH domain) consisting of a sequence having at least 80% identity to an amino acid sequence of any one of SEQ ID NOs: 3 to 5.

The light chain variable domain may consist of an amino acid sequence having at least 80%, preferably at least 90%, more preferably at least 95%, and most preferably at least 99% identity to an amino acid sequence of SEQ ID NO: 1.

The heavy chain variable domain may consist of an amino acid sequence having at least 80%, preferably at least 90%, more preferably at least 95%, and most preferably at least 99% identity to an amino acid sequence of any one of SEQ ID NOs: 3 to 5.

An antibody comprising the light chain variable domain and the heavy chain variable domain may specifically bind to mesothelin (MSLN). Here, the MSLN to which the antibody binds may be human MSLN. That is, the antibody may specifically bind to human-derived MSLN or cancer cells attached thereto.

As used herein, the term "MSLN" may refer to a concept that collectively refers to MSLN itself, and any variant, isotype, and paralog thereof, which are present in an animal and preferably in a human and a monkey. In addition, as used herein, the term "human MSLN" refers to human-derived MSLN. As used herein, the term "mouse MSLN" refers to mouse-derived MSLN.

As used herein, the term "antibody" refers to an immunoglobulin (Ig) molecule that is immunologically reactive with a particular antigen, that is, a protein molecule that acts as a receptor that specifically recognizes an antigen. In addition, the antibody may be a whole antibody or an antibody fragment.

In the light and heavy chain variable domains, some amino acids may be substituted, inserted, and/or deleted as long as properties consistent with the object of the present invention, such as affinity and specificity to MSLN, are maintained. For example, conservative substitutions of amino acids may occur in the light and/or heavy chain variable domains. The conservative substitution means a substitution of an original amino acid sequence with another amino acid residue having properties similar thereto.

For example, lysine, arginine, and histidine have similar properties in that they have a basic side chain, and aspartic acid and glutamic acid have similar properties in that they have an acidic side chain. In addition, glycine, asparagine, glutamine, serine, threonine, tyrosine, cysteine, and tryptophan have similar properties in that they have a non-charged polar side chain; alanine, valine, leucine, threonine, isoleucine, proline, phenylalanine, and methionine have similar properties in that they have a nonpolar side chain; and tyrosine, phenylalanine, tryptophan, and histidine have similar properties in that they have an aromatic side chain.

Therefore, it is apparent to those skilled in the art that the amino acid substitutions within the group of the amino acids having similar properties as described above will not cause any significant change in the properties. For this reason, antibodies that have undergone variation caused by a conservative substitution within the variable domain are also included in the scope of the present invention as long as such antibodies maintain properties of the antibody of the present invention.

On the other hand, the antibody may specifically bind to cancer cells expressing MSLN, specifically to the surface of the cancer cells, through specific binding to MSLN. Here, the cancer cells expressing MSLN may include, but are not limited to, human cancer cells.

The light and heavy chain variable domains of the antibody may consist of complementarity determining regions (CDRs) and framework regions (FRs). Typically, CDRs provide binding specificity to specific antigens, and FRs function to form the antibody's folded structure, to support binding of CDRs, or the like.

The antibody may be an antibody that has, as a backbone, the CDR amino acid sequence of the existing mouse anti-MSLN antibody, MI323, and the amino acid sequence of FRs and constant domain (Fc) of a human antibody similar to MI323, in which some amino acid residues of the CDR and FR portions are in a form of being substituted so that these residues can specifically bind to a human.

The antibody may comprise a light chain CDR1 including the amino acid sequence of SEQ ID NO: 9; a light chain CDR2 including the amino acid sequence of SEQ ID NO: 10; a light chain CDR3 including the amino acid sequence of SEQ ID NO: 11; a heavy chain CDR1 including an amino acid sequence of any one selected from the group consisting of SEQ ID NOs: 12 to 14; a heavy chain CDR2 including the amino acid sequence of any one selected from the group consisting of SEQ ID NOs: 15 to 17; and a heavy chain CDR3 including the amino acid sequence of SEQ ID NO: 18.

In an embodiment, the antibody may comprise a light chain CDR1 including the amino acid sequence of SEQ ID NO: 9; a light chain CDR2 including the amino acid sequence of SEQ ID NO: 10; a light chain CDR3 including the amino acid sequence of SEQ ID NO: 11; a heavy chain CDR1 including the amino acid sequence of SEQ ID NO: 12; a heavy chain CDR2 including the amino acid sequence of SEQ ID NO: 15; and a heavy chain CDR3 including the amino acid sequence of SEQ ID NO: 18.

The antibody may comprise a light chain CDR1 including the amino acid sequence of SEQ ID NO: 9; a light chain CDR2 including the amino acid sequence of SEQ ID NO: 10; a light chain CDR3 including the amino acid sequence of SEQ ID NO: 11; a heavy chain CDR1 including the amino acid sequence of SEQ ID NO: 13; a heavy chain CDR2 including the amino acid sequence of SEQ ID NO: 16; and a heavy chain CDR3 including the amino acid sequence of SEQ ID NO: 18.

The antibody may comprise a light chain CDR1 including the amino acid sequence of SEQ ID NO: 9; a light chain CDR2 including the amino acid sequence of SEQ ID NO: 10; a light chain CDR3 including the amino acid sequence of SEQ ID NO: 11; a heavy chain CDR1 including the amino acid sequence of SEQ ID NO: 14; a heavy chain CDR2 including the amino acid sequence of SEQ ID NO: 17; and a heavy chain CDR3 including the amino acid sequence of SEQ ID NO: 18.

Accordingly, the antibody may be a humanized antibody that specifically binds to human MSLN. As used herein, the term "humanized antibody" refers to a chimeric antibody that contains a minimal sequence derived from an immunoglobulin of a non-human antibody, such as a mouse antibody, and may mean such an antibody in which all parts except the sequence corresponding to a hypervariable region are substituted with their human counterparts.

In addition, the term "hypervariable region (HVR)" refers to a region of a variable domain which exhibits hypervariability or forms a structurally defined loop in the sequence of an antibody. Among definitions identifying the same, the complementarity determining region (CDR) definition according to Kabat is most commonly used to classify regions based on sequence variability.

An antibody fragment of the antibody may also be used as long as the antibody fragment maintains the antibody's function. The antibody or antibody fragment may include, but is not limited to, single-chain antibodies, diabodies, triabodies, tetrabodies, Fab fragments, F(ab')2 fragments, Fd's, scFv's, domain antibodies, minibodies, scAb's, IgD antibodies, IgE antibodies, IgM antibodies, IgG1 antibodies, IgG2 antibodies, IgG3 antibodies, IgG4 antibodies, derivatives of antibody's constant domains, artificial antibodies based on protein scaffolds, and the like, which maintain a binding function to MSLN.

The antibody may also be used in the form of an antibody-drug conjugate (ADC) obtained by binding of the antibody with an anticancer drug having tumor-cell proliferation inhibition efficacy. As used herein, the term "anticancer" includes "prevention" and "treatment" effects on cancer, and the "prevention" means any act of inhibiting or delaying cancer. In addition, the "treatment" means any act of ameliorating or beneficially altering symptoms of cancer.

The drug that can be used in the antibody-drug conjugate includes any compound having a cytotoxic or cytostatic effect, and a part or functional group of the compound. Examples of the drug include microtubulin structure formation inhibitors, meiosis inhibitors, RNA polymerase inhibitors, topoisomerase inhibitors, DNA intercalators, DNA alkylators, ribosomal inhibitors, miRNAs, shRNAs, siRNAs, radioisotopes, and toxins, among which at least one compound may be used.

The drug may include, but is not limited to, maytansinoid, auristatin, dolastatin, trichothecene, CC1065 (NSC 298223), calicheamicin, taxane, anthracycline, methotrexate, adriamycin, vindesine, vinca alkaloids (vincristine, vinblastine, etoposide), doxorubicin, melphalan, mitomycin C, chlorambucil, daunorubicin, daunomycin, etoposide, teniposide, carminomycin, aminopterin, dactinomycin, mitomycins, bleomycins, esperamicins, other enediyne antibiotics, 5-fluorouracil, other nitrogen mustards and stereoisomers, isosteres, homologs, or derivatives thereof, cis-platinum and cis-platinum homologs, other intercalator enzymes and fragments thereof, for example, nucleases, antibiotics, toxins (enzymatically active toxins or small molecule toxins of bacterial, fungal, plant, or animal origin), and various antitumor or anticancer agents such as cisplatin, CPT-11, paclitaxel, and docetaxel.

In addition, the radioisotope (radionuclide) includes 3H, 14C, 32P, 35S, 36Cl, 51Cr, 57Co, 58Co, 59Fe, 90Y, 125I, 131I, 186Re, and the like. MicroRNAs (miRNAs), siRNAs, shRNAs, and the like may also be used which can inhibit expression of certain oncogenes.

Binding of the anti-MSLN antibody with a drug is preferably achieved by conjugation using a functional group such as a thiol group of an amino acid residue such as lysine or cysteine in the antibody. If necessary, it is also possible to perform conjugation in a linker-mediated form which is commonly used. A maleimide- or iodine acetamide-based linker may also be used.

When a drug is conjugated to the antibody or a fragment thereof, the drug may be conjugated to the C-terminal site, which is opposite to an antigen binding site, from the viewpoint of decreasing an effect on the antibody or fragment's binding capacity and specificity to MSLN, and the like. When the whole antibody, rather than a fragment thereof, is used, the drug may be conjugated to an Fc region.

In addition, the antibody may also be used as a chimeric antigen receptor (CAR)-based therapeutic agent containing the same. Examples of such a therapeutic agent preferably include, but are not limited to, chimeric antigen receptor T cell (CAR-T cell) or chimeric antigen receptor natural killer cell (CAR-NK cell) therapeutics.

The antibody may also be used in the form of a bispecific antibody containing an anti-MSLN antibody. The bispecific antibody is an antibody that has capacity of binding to two antigens at the same time, and may typically exist in a form in which heavy and light chain pairs that bind to different antigens are linked to each other.

In addition, the bispecific antibody is available in a form such as a bispecific single-chain antibody where single-chain antibody fragments (scFv's), in which VL and VH are linked to each other via a short linker peptide, are connected in the form of scFv1-scFv2(-Fc), a single-domain antibody (sdAb)-based dual antibody using VH, and a bispecific antibody generated using BiTE technology (see www.micromet.de) from Micromet, Germany.

The bispecific antibody may exist in a form in which the anti-MSLN antibody is bound to an antibody or a fragment thereof having binding capacity to an immunopotent cell-specific target molecule. The immunopotent cell-specific target molecule may preferably be selected from, but is not limited to, TCR/CD3, CD16 (FcγRIIIa), CD44, CD56, CD69, CD64 (FcγRI), CD89, and CD11b/CD18 (CR3).

In another aspect of the present invention, there is provided a polynucleotide encoding the light chain variable domain (VL domain) and the heavy chain variable domain (VH domain) of the antibody according to the present invention and an expression vector comprising the same.

The polynucleotide that encodes the heavy chain variable domain of the antibody or an antibody fragment, that is, gene, may be easily derived by those skilled in the art from the amino acid sequence of the anti-MSLN antibody.

As used herein, the term "expression vector" refers to a recombinant vector capable of expressing a target protein in a host cell, and means a gene construct that contains essential regulatory elements operably linked thereto so that an inserted gene is expressed. The gene encoding the anti-MSLN antibody may be inserted into a separate vector or may be used in a form of being inserted into the same vector.

Specifically, the polynucleotide that encodes the amino acid sequence of the anti-MSLN antibody may be used in a form of being inserted into a separate or the same vector, and the polynucleotide that encodes the heavy chain or a variable domain thereof may be used in a form of being inserted into a separate or the same vector.

As used herein, the term "operably linked" means that a nucleic acid expression regulatory sequence and a nucleic acid sequence encoding a desired protein are functionally linked to perform a desired function. Operable linkage with a recombinant vector may be achieved using genetic recombination techniques well known in the art, and site specific DNA cleavage and ligation may be easily achieved using enzymes and the like commonly known in the art.

Expression vectors suitable for production of the anti-MSLN antibody may contain signal sequences for membrane targeting or secretion in addition to expression regulatory elements such as promoters, initiation codons, termination codons, polyadenylation signals, and enhancers. Initiation codons and termination codons are generally considered to be part of a nucleotide sequence encoding an immunogenic target protein. Such codons must be functional in a subject when a gene construct is administered and must be in frame with a coding sequence. In general, promoters may be constitutive or inducible. The promoter may include, but is not limited to, prokaryotic promoters such as lac, tac, T3, and T7, simian virus 40 (SV40) promoters, mouse breast tumor virus (MMTV) promoters, human immunodeficiency virus (HIV) promoters, for example, long terminal repeat (LTR) promoter of HIV, Moloney virus promoters, cytomegalovirus (CMV) promoters, Epstein bar virus (EBV) promoters, Rous sarcoma virus (RSV) promoters, as well as β-actin promoters, human hemoglobin-, human muscle creatine-, human metallothionein-derived eukaryotic promoters, and the like.

The expression vector may further contain a selectable marker that allows for selection of host cells containing the same. The selectable marker is employed for selecting cells transformed with the vector. For the selectable marker, markers may be used which confer a selectable phenotype, such as drug resistance, auxotrophy, resistance to cytotoxic agents, or expression of surface proteins. In an environment treated with a selective agent, only cells expressing a selection marker survive, which allows for selection of transformed cells. In addition, when the vector is a replicable expression vector, such a vector may contain a replication origin that is a specific nucleic acid sequence from which replication is initiated.

As a recombinant expression vector for insertion of a foreign gene, various forms of vectors such as plasmids, viruses, and cosmids may be used. The type of recombinant vector is not particularly limited as long as the vector functions to express a desired gene and produce a desired protein in various host cells including prokaryotic and/or eukaryotic cells. The vector may preferably be a vector capable of producing a large amount of foreign protein that is in a form similar to its natural state while having a promoter with strong activity and strong expression capacity.

Various expression host/vector combinations may be used to express the anti-MSLN antibody. The expression vector suitable for eukaryotic hosts includes, but is not limited to, expression regulatory sequences derived from SV40, bovine papillomavirus, adenovirus, adeno-associated virus, cytomegalovirus, and retrovirus. The expression vector that may be used in bacterial hosts includes bacterial plasmids obtained from *Escherichia coli*, such as pET, pRSET, pBluescript, pGEX2T, pUC vector, colEl, pCR1, pBR322, pMB9, and derivatives thereof; plasmids having a wide host range such as RP4; phage DNAs that may be exemplified by a wide variety of phage lambda derivatives such as λgt10, λgt11, and NM989; and other DNA phages such as M13 and filamentous single-stranded DNA phages. The expression vector useful for yeast cells may include 2-micron plasmids and derivatives thereof. The vector useful for insect cells may be pVL941.

In yet another aspect of the present invention, there is provided a host cell, transformed with an expression vector according to the present invention. The expression vector may be inserted into a host cell to form a transformant. A suitable host cell for the vector may include prokaryotic cells such as *Escherichia coli, Bacillus subtilis, Streptomyces* sp., *Pseudomonas* sp., *Proteus mirabilis*, or *Staphylococcus* sp. In addition, the host cell may include eukaryotic cells including lower eukaryotic cells from fungi such as *Aspergillus* sp., yeasts such as *Pichia pastoris, Saccharomyces cerevisiae, Schizosaccharomyces* sp., and *Neurospora crassa*, and other lower eukaryotes, and higher eukaryotic cells such as insect cells. In addition, the host cell may also be derived from plants or mammals. Preferably, the host cell that may be used includes, but is not limited to, monkey kidney cells (COS7 cells), NSO cells (myeloma cells of mouse origin), SP2/0 cells (myeloma cells of mouse origin), other myeloma cell lines, Chinese hamster ovary (CHO) cells, W138 cells (diploid human cell culture), baby hamster kidney (BHK) cells, MDCK, HuT 78 cells, HEK293 cells, and the like, with CHO cells being preferred.

As used herein, the term "transformation into host cells" is intended to include any method for introducing a nucleic acid into an organism, cell, tissue, or organ and, and such transformation may be performed using a standard technique as known in the art selected depending on the type of host cell. Specifically, electroporation, protoplast fusion, calcium phosphate ($CaPO_4$) precipitation, calcium chloride ($CaCl_2$)) precipitation, agitation using silicon carbide fiber, *Agrobacterium*-mediated transformation, PEG-, dextran sulfate-, lipofectamine-, or desiccation/inhibition-mediated transformation, or the like may be used. However, the present invention is not limited thereto.

In still yet another aspect of the present invention, there is provided a method for producing an antibody that specifically binds to MSLN, comprising culturing the host cell. Specifically, the method for producing an antibody may comprise the steps of: inserting into a vector, a nucleotide sequence encoding the anti-MSLN antibody, to construct a recombinant vector; transforming a host cell with the recombinant vector into and performing culture; and separating and purifying a humanized antibody from the cultured transformant.

The humanized antibodies may be produced in a large amount by culturing the transformant, in which the recombinant vector is expressed, in a nutrient medium, and the medium and culture conditions may be appropriately selected from those known in the art depending on the type of host cell. During culture, conditions such as temperature, pH of a medium, and culture time may be appropriately adjusted to be suitable for cell growth and mass production of a protein.

The recombinantly produced anti-MSLN antibodies as described above may be recovered from a medium or a cell lysate. When the antibody is in a membrane-bound form, such an antibody may be liberated from the membrane using a suitable surfactant solution (for example, Triton-X 100) or by enzymatic cleavage. Cells used for expression of humanized antibodies may be disrupted by various physical and chemical means such as freeze-thaw cycles, sonication, mechanical disruption, or cell lysis agents, and separation and purification may be performed using conventional biochemical separation techniques. The biochemical separation technique that may be used includes, but is not limited to, electrophoresis, centrifugation, gel filtration, precipitation, dialysis, chromatography (ion-exchange chromatography, affinity chromatography, immunoabsorbent chromatography, size exclusion chromatography, or the like), isoelectric focusing, and the like.

In still yet another aspect of the present invention, there is provided a pharmaceutical composition for preventing or treating cancer, comprising an antibody according to the present invention or a fragment thereof.

The type of cancer that can be treated with the pharmaceutical composition may include both solid cancer and blood cancer, and preferably may include, but is not limited to, any cancers which express MSLN, such as mesothelioma, pancreatic cancer, ovarian cancer, gastric cancer, lung cancer, or endometrial cancer.

The pharmaceutical composition may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration.

Formulation of a pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms.

In addition, the pharmaceutical composition may contain a surfactant that can improve membrane permeability. These surfactants may be derived from steroids or may include cationic lipids such as N-[1-(2,3-dioleoyl)propyl-N,N,N-trimethylammonium chloride (DOTMA), or various compounds such as cholesterol hemisuccinate and phosphatidyl glycerol. However, the surfactant is not limited thereto.

In still yet another aspect of the present invention, there is provided a method for treating cancer or inhibiting cancer growth, comprising administering the pharmaceutical composition to a subject. The pharmaceutical composition comprising the anti-MSLN antibody may be administered in a pharmaceutically effective amount to treat cancer cells or metastases thereof or to inhibit cancer growth. The effective amount may vary depending on various factors such as type of cancer, the patient's age, weight, nature and severity of symptoms, type of current therapy, number of treatments, dosage form, and route of administration, and may be easily determined by experts in the corresponding field.

The pharmaceutical composition may be administered together or sequentially with the above-mentioned pharmacological or physiological components, and may also be administered in combination with additional conventional therapeutic agents, in which case the pharmaceutical composition may be administered sequentially or simultaneously with the conventional therapeutic agents. Such administration may be single or multiple administration. Taking all of the above factors into consideration, it is important to administer an amount that is a minimum amount and allows the maximum effect to be obtained without side effects, and such an amount may be easily determined by those skilled in the art.

As used herein, the term "subject" refers to a mammal, preferably human, suffering from or at risk of a condition or disease that can be alleviated, inhibited, or treated by administration of the pharmaceutical composition.

As used herein, the term "administration" means introducing a predetermined substance into a subject in any suitable manner, and the pharmaceutical composition may be administered via any route as long as the route allows the pharmaceutical composition to reach a target tissue. Such an administration method may include, but is not limited to, intraperitoneal administration, intravenous administration, intramuscular administration, subcutaneous administration, intradermal administration, oral administration, topical administration, intranasal administration, pulmonary administration, or rectal administration. Here, in case of being orally administered, from the viewpoint that proteins are digested, it may be desirable to formulate a composition for oral use so that an active agent is coated or the composition is protected from digestion in the stomach. In addition, the pharmaceutical composition may be administered by any device such that an active ingredient can migrate to its target cell.

In still yet another aspect of the present invention, there is provided a use of the antibody of the present invention for preventing or treating cancer.

In still yet another aspect of the present invention, there is provided a use of the antibody of the present invention for manufacture of a medicament for preventing or treating cancer.

In still yet another aspect of the present invention, there is provided a method for preventing or treating cancer, comprising administering the antibody of the present invention to a subject.

BEST MODE FOR CARRYING OUT THE INVENTION

Hereinafter, the present invention will be described in more detail by way of examples. The following examples are described for the purpose of illustrating the present invention, and the scope of the present invention is not limited thereto.

Example 1. Production of Humanized Anti-MSLN Antibodies

Example 1.1. Selection of Candidate Antibodies for Humanization

The amino acid sequences of the light chain variable domain (VL domain) and heavy chain variable domain (VH domain) of mouse MI323, known as an anti-MSLN antibody, were entered into a web-based database (IgBLAST), and then the most similar human embryonic antibody sequences were searched. As a result, the highest amino acid sequence similarity was shown between the light chain variable region of mouse MI323 and *Homo sapiens* IGKV7-39*01 (IMGT gene name), and between the heavy chain variable domain of mouse MI323 and *Homo sapiens* IGHV1-3*01 (IMGT gene name).

Example 1.2. Humanization of Light Chain Variable Domain

The CDR amino acid sequence of *Homo sapiens* IGKV7-39*01 (IMGT gene name), a human embryonic antibody having a sequence most similar to the light chain variable domain of MI323, was replaced with the CDR sequence of mouse MI323, to prepare a partially humanized light chain variable domain of MI323.

In order to enhance antigen-binding properties of the partially humanized light chain variable domain of MI323, amino acid residues in the CDR sequences that are thought to play an important function in antigen-binding properties were replaced with the same amino acid residues as *Homo sapiens* IGKV7-39*01 (IMGT gene name). The amino acid sequence of the humanized light chain variable domain of MI323 thus prepared is shown in Table 1 below.

Referring to Table 1, the humanized light chain variable domain of MI323 was prepared by changing the 24$^{th}$ amino acid residue in the light chain variable domain of mouse MI323 from lysine (K) to arginine (R). Here, the light chain variable domain of mouse MI323 was used as a control for comparison of affinity to an MSLN antigen.

TABLE 1

| Clone | Variable domain | Amino acid sequence (Parts in bold indicate light chain CDR1, CDR2, CDR3 in order) | SEQ ID NO |
|---|---|---|---|
| VL-1 | Light chain | DIQMTQSPSSLSASVGDRVTITCRASQDV STAVAWYQQKPGKAPKLLIYSASYRYPGV PSRFSGSGSGTDFTLTISSLQPEDFATYYC QQHYSTPWTFGGGTKLEIKR | 1 |
| MI 323 | Light chain | DIVMTQSHKFMSTSVGDRVSITCRASQDV STAVAWYQQKPGQSPKLLIYSASYRYPGV PDRFTGSGSGTDFTFTISSVQAEDLALYYC QQHYSTPWTFGGGTKLEIKR | 2 |

Example 1.3. Humanization of Heavy Chain Variable Domain

The CDR amino acid sequence of *Homo sapiens* IGHV1-3*01 (IMGT gene name), a human embryonic antibody having a sequence most similar to the heavy chain variable domain of MI323, was replaced with the CDR sequence of mouse MI323, to prepare a partially humanized heavy chain variable domain of MI323.

In order to enhance antigen-binding properties of the partially humanized heavy chain variable domain of MI323, amino acid residues in the CDR and framework region (FR) sequences that are thought to play an important function in antigen-binding properties were replaced with the same amino acid residues as mouse MI323. The amino acid sequence of the humanized heavy chain variable domain of MI323 thus prepared is shown in Table 2 below.

Referring to Table 2, random modifications were made to amino acid residues in the CDRs and FRs of the heavy chain variable domain of mouse MI323, to prepare a total of 3 humanized heavy chain variable domains of MI323. Here, the heavy chain variable domain of mouse MI323 was used as a control for comparison of affinity to an MSLN antigen.

TABLE 2

| Clone | Variable domain | Amino acid sequence (Parts in bold indicate light chain CDR1, CDR2, CDR3 in order) | SEQ ID NO |
|---|---|---|---|
| VH-1 | Heavy chain | QVQLVQSGAEVKKPGASVKVSCKASGYSFTS YFMHWVRQAPGQRLEWMGWIFPGNGNTKYSQ KFQGRVTITRDTSASTAYMELSSLRSEDTAV YYCARSGGYQYYFDYWGQGTLVTVSS | 3 |
| VH-2 | Heavy chain | QVQLVQSGAEVKKPGSSVKVSCKASGYSFTS YFISWVRQAPGQGLEWMGGIFPGSGNANYAQ KFQGRVTITADESTSTAYMELSSLRSEDTAV YYCARSGGYQYYFDYWGQGTLVTVSS | 4 |

TABLE 2-continued

| Clone | Variable domain | Amino acid sequence (Parts in bold indicate light chain CDR1, CDR2, CDR3 in order) | SEQ ID NO |
|---|---|---|---|
| VH-3 | Heavy chain | EVQLVQSGAEVKKPGTSVKVSCKASGYSFTS YFIQWVRQAPGQGLEWIGWIFPGSGNTKYSQ KFQGRVTITRDTSTSTAYMELSSLRSEDTAV YYCARSGGYQYYFDYWGQGTLVTVSS | 5 |
| MI 323 | Heavy chain | EVQLQQSGPELVKPGTSVKISCKASGYSFTS YFIQWVKQRPGQGLEWIGWIFPGSGNTKYNE MFKGKATLAADTSSSTAYMQLSSLTSEDSAV YFCARSGGYQYYFDYWGQGTSVTVSS | 6 |

Example 1.4. Cloning of Humanized Anti-MSLN Antibodies

Each of the gene for one light chain variable domain (VL-1) as prepared above and the gene for the light chain variable domain of MI323 was inserted into pcDNA3.4 animal cell expression vector containing a kappa light chain constant domain (κCL). In addition, each of the genes for 3 heavy chain variable domains (VH-1, VH-2, VH-3) and the gene for the heavy chain variable domain of MI323 was inserted into pcDNA3.4 animal cell expression vector containing IgG1 constant domains (CH1, hinge, CH2, CH3).

The respective specific amino acid sequences for the kappa light chain constant domain and the IgG1 heavy chain constant domain are shown in Table 3 below.

TABLE 3

| Clone | Constant domain | Amino acid sequence | SEQ ID NO |
|---|---|---|---|
| κ | Light chain | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC | 7 |
| IgG1 | Heavy chain | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSRDELTKNQVSLTCLVKGFY PSDIAVEWESNGQPENNYKTTPPVLDSDGSFF LYSKLTVDKSRWQQGNVFSCSVMHEALHNHYT QKSLSLSPGK | 8 |

Example 1.5. Transfection of Humanized Anti-MSLN Antibodies

Twenty-four hours before transfection, Expi293F cells at a density of 2.0×10$^6$ cells/ml were passaged with Expi293 medium at 125±10 rpm in a shaking incubator at a condition of 37° C. and 8% $CO_2$. When transfection was performed, the number of cells and cell viability were measured to identify whether cell viability of 95% or higher was exhibited.

The cells were dispensed at 7.5×10$^7$ cells in a 125 mL culture flask, and then Expi293 medium was added to adjust the final volume to 25 mL (based on 30 mL). Using Opti-MEM I medium, 30 μg of antibody-expressing vector was mixed therewith to a total of 1.5 ml and incubation was performed for 5 minutes at room temperature. For the antibody vectors, a total of 3 humanized MI323 IgG1 antibodies, obtained by combination of the expression vector for one light chain variable domain and the expression vectors for 3 heavy chain variable domains, were used. A mouse human chimeric MI323 IgG1 antibody was used as a control antibody vector.

Using Opti-MEM I medium, 80 μl of transfection reagent was mixed therewith to a total of 1.5 ml and incubation was performed for 5 minutes at room temperature. The Opti-MEM I media respectively containing the vector and the transfection reagent were gently mixed and allowed to react at room temperature for 20 minutes. Then, the resultant was placed in the flask containing Expi293F cells. Incubation was performed at 125±10 rpm for 16 to 20 hours in a shaking incubator at a condition of 37° C. and 8% $CO_2$. Then, 1.5 ml of transfection enhancer I and 150 μl of transfection enhancer II were added thereto, and incubation was performed for 6 days to obtain antibodies.

Example 1.6. Purification of Antibodies

The incubation was centrifuged at 4,000 rpm for 30 minutes, filtered through a 0.22 μm filter, and then cell debris was removed to obtain the supernatant. 0.2 ml of Mabselect Xtra resin was added to a column, and equilibration was performed using Protein A binding buffer in a volume corresponding to 10 times the resin volume.

Subsequently, the supernatant was loaded onto the column using gravity. After the loading was completed, the column was washed with Protein A binding buffer in a volume corresponding to 10 times the resin volume.

Then, IgG elution buffer was added to the column and elution was performed. The eluate was neutralized by adding 25 μl of 1.5 M Tris-Cl per 1 ml of the eluate. Then, the eluate concentration was measured at an OD of 280 nm. The eluant for which the concentration had been measured was subjected to buffer exchange with PBS via dialysis.

Example 2. Measurement of Affinity to Recombinant MSLN of Humanized Anti-MSLN Antibodies The Octet system was used to measure affinity to recombinant MSLN of the humanized anti-MSLN antibodies (HMI323) produced in accordance with Example 1. The "HMI323" refers to "humanized MI323".

Specifically, recombinant human MSLN was prepared at a concentration of 5 μg/ml in 1× kinetic buffer and used to treat a 96-well-plate at 200 μl/well. The MSLN after treatment was fixed to the anti-Penta His (HIS1K, Cat #18-5121, Fortebio) sensor.

Then, the 3 humanized anti-MSLN antibodies produced in accordance with Example 1 and the mouse human chimeric MI323 IgG1 clones were diluted to a concentration of 50, 25, 12.5, 6.25, or 3.125 nM in 1× kinetic buffer, and treatment therewith was performed at 200 μl/well. For the 1×kinetic buffer, one obtained by 10-fold dilution of 10×kinetic buffer (ForteBio, Cat #18-1092) with PBS was used.

The interaction between the MSLN fixed to the sensor and the antibody at several concentrations was analyzed to calculate antigen-antibody affinity, and the results are shown in Table 4 below.

TABLE 4

| Clone | ka (1/M · s) | kd (1/s) | KD (nM) |
|---|---|---|---|
| MI323 | $4.54 \times 10^5$ | $1.30 \times 10^{-5}$ | 0.0286 |
| HMI323VL-1/HMI323VH-1 | $6.65 \times 10^5$ | $9.25 \times 10^{-5}$ | 0.139 |
| HMI323VL-1/HMI323VH-2 | $1.86 \times 10^6$ | $5.09 \times 10^{-4}$ | 0.273 |
| HMI323VL-1/HMI323VH-3 | $8.42 \times 10^5$ | $2.75 \times 10^{-5}$ | 0.0327 |

As can be seen from the results in Table 4, it was found that the combination of HMI323VL-1/HMI323VH-3 maintains the closest affinity to MI323, and it was identified that the other two clones show a slightly decreased affinity as compared with the MI323 antibody but overall maintain high affinity to MSLN.

Example 3. Measurement of Affinity to MSLN Expressed on Cancer Cell Surface of Humanized Anti-MSLN Antibodies Flow cytometry was used to identify whether the humanized anti-MSLN antibodies (HMI323) produced in accordance with Example 1 also show affinity to MSLN expressed on the cancer cell surface.

Specifically, each of H226 (mesothelioma), AsPC-1 (pancreatic cancer), Capan-2 (pancreatic cancer), and PL45 (pancreatic cancer) cell lines was centrifuged at 1,500 rpm for 5 minutes, and then washing with FACS buffer (PBS containing 3% FBS) was performed three times. Subsequently, the respective cancer cells at a concentration of $3 \times 10^6$ cells/ml were diluted with FACS buffer and were used at 100 μl to treat each well of a 96-well-plate.

Then, each of mouse/human chimeric MI323 IgG1 and HMI323VL-1/HMI323VH-3 IgG1 antibody was added to each well at a concentration of 5 μg/ml, mixed with the cells, and then incubated at 4° C. for 1 hour. Subsequently, centrifugation was performed at 1,500 rpm for 5 minutes, and then the supernatant was discarded. A process, in which 200 μl of FACS buffer was added thereto for resuspension and washing of the cells, was repeated three times.

Then, a process, in which a phycoerythrin (PE)-conjugated human IgG antibody was diluted 500-fold in FACS buffer and used to wash the cells, was repeated three times. The washed cells were fixed with 100 μl of BD Cytofix™, and the mean fluorescence intensity (MFI) of each sample was analyzed with the LSRFortessa™ (flow cytometer) instrument. The analysis results are illustrated in FIGS. 1 to 8.

Referring to FIGS. 1 to 8, it was found that all antibodies, which had bound to recombinant human MSLN, also specifically bound to human MSLN-expressing cancer cells.

Although the embodiments have been described by a limited number of examples and the drawings as described above, it will be apparent to those skilled in the art that various changes and modifications may be made without departing from the spirit and scope of the invention. For example, it is possible to achieve desired results even in a case where the techniques as described are performed in a different order than the described method, and/or the components as described are assembled or combined in a different form than the described method, or replaced or substituted by other components or equivalents.

Therefore, other implementations, other embodiments, and equivalents of the appended claims fall within the scope of the appended claims.

The invention claimed is:

1. An antibody that specifically binds to mesothelin (MSLN), comprising: a light chain variable domain (VL domain) comprising the amino acid sequence of SEQ ID NO: 1; and a heavy chain variable domain (VH domain) comprising the amino acid sequence of any one of SEQ ID NOs: 3 to 5.

2. The antibody of claim 1, wherein the MSLN is human MSLN.

3. The antibody of claim 1, wherein the antibody specifically binds to a mesothelin (MSLN)-expressing cancer cell.

4. The antibody of claim 3, wherein the MSLN-expressing cancer cell is a human cancer cell.

5. The antibody of claim 1, wherein the antibody is a humanized antibody.

6. A polynucleotide that encodes the light chain variable domain (VL domain) and the heavy chain variable domain (VH domain) of the antibody of claim 1.

7. An expression vector comprising the polynucleotide of claim 6.

8. A host cell transformed with the expression vector of claim 7.

9. A method for producing an antibody that specifically binds to mesothelin (MSLN), comprising culturing the host cell of claim 8.

10. A pharmaceutical composition comprising the antibody of claim 1 or an antigen-binding fragment thereof.

11. A method for treating cancer in a subject, comprising administering an effective amount of the antibody of claim 1 to the subject.

12. The method of claim 11, wherein the cancer is mesothelioma, pancreatic cancer, ovarian cancer, gastric cancer, lung cancer, or endometrial cancer.

13. The method of claim 11, wherein the antibody is a humanized antibody.

* * * * *

SEQUENCE LISTING

<160> NUMBER OF SEQ ID NOS: 18

<210> SEQ ID NO 1
<211> LENGTH: 108
<212> TYPE: PRT
<213> ORGANISM: Artificial Sequence
<220> FEATURE:
<223> OTHER INFORMATION: VL-1 clone of humanized MI323

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Leu Glu Ile Lys Arg
            100                 105
```

<210> SEQ ID NO 2
<211> LENGTH: 108
<212> TYPE: PRT
<213> ORGANISM: Artificial Sequence
<220> FEATURE:
<223> OTHER INFORMATION: VL domain of mouse MI323

<400> SEQUENCE: 2

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Pro Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg
            100                 105
```

<210> SEQ ID NO 3
<211> LENGTH: 119
<212> TYPE: PRT
<213> ORGANISM: Artificial Sequence
<220> FEATURE:
<223> OTHER INFORMATION: VH-1 clone of humanized MI323

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30
```

Phe Met His Trp Val Arg Gln Ala Pro Gly Gln Arg Leu Glu Trp Met
        35                  40                  45

Gly Trp Ile Phe Pro Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Gln Tyr Tyr Phe Asp Tyr Trp Gly Gln Gly
            100                 105                 110

Thr Leu Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: VH-2 clone of humanized MI323

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
            20                  25                  30

Phe Ile Ser Trp Val Arg Gln Ala Pro Gly Gln Gly Leu Glu Trp Met
        35                  40                  45

Gly Gly Ile Phe Pro Gly Ser Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Gln Tyr Tyr Phe Asp Tyr Trp Gly Gln Gly
            100                 105                 110

Thr Leu Val Thr Val Ser Ser
        115

<210> SEQ ID NO 5
<211> LENGTH: 119
<212> TYPE: PRT
<213> ORGANISM: Artificial Sequence
<220> FEATURE:
<223> OTHER INFORMATION: VH-3 clone of humanized MI323

<400> SEQUENCE: 5

Glu Val Gln Leu Val Gln Ser Gly Ala Glu Val Lys Lys Pro Gly Thr
1               5                   10                  15

Ser Val Lys Val Ser Cys Lys Ala Ser Gly Tyr Ser Phe Thr Ser Tyr
            20                  25                  30

Phe Ile Gln Trp Val Arg Gln Ala Pro Gly Gln Gly Leu Glu Trp Ile
        35                  40                  45

Gly Trp Ile Phe Pro Gly Ser Gly Asn Thr Lys Tyr Ser Gln Lys Phe
    50                  55                  60

Gln Gly Arg Val Thr Ile Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys 85                  90                  95

Ala Arg Ser Gly Gly Tyr Gln Tyr Tyr Phe Asp Tyr Trp Gly Gln Gly
                100                 105                 110

Thr Leu Val Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: VH domain of mouse MI323

<400> SEQUENCE: 6

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Ser Phe Thr Ser Tyr
                20                  25                  30

Phe Ile Gln Trp Val Lys Gln Arg Pro Gly Gln Gly Leu Glu Trp Ile
            35                  40                  45

Gly Trp Ile Phe Pro Gly Ser Gly Asn Thr Lys Tyr Asn Glu Met Phe
    50                  55                  60

Lys Gly Lys Ala Thr Leu Ala Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Gly Gly Tyr Gln Tyr Tyr Phe Asp Tyr Trp Gly Gln Gly
                100                 105                 110

Thr Ser Val Thr Val Ser Ser
        115

<210> SEQ ID NO 7
<211> LENGTH: 106
<212> TYPE: PRT
<213> ORGANISM: Artificial Sequence
<220> FEATURE:
<223> OTHER INFORMATION: kappa CL domain

<400> SEQUENCE: 7

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 8
<211> LENGTH: 330
<212> TYPE: PRT
<213> ORGANISM: Artificial Sequence
<220> FEATURE:

<223> OTHER INFORMATION: IgG1 CH domain

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 11
<212> TYPE: PRT
<213> ORGANISM: Artificial Sequence
<220> FEATURE:
<223> OTHER INFORMATION: Amino acid seqeunce for anti-MSLN antibody of
      CDR1 (VL)

<400> SEQUENCE: 9

Arg Ala Ser Gln Asp Val Ser Thr Ala Val Ala

<210> SEQ ID NO 10
<211> LENGTH: 7
<212> TYPE: PRT
<213> ORGANISM: Artificial Sequence
<220> FEATURE:
<223> OTHER INFORMATION: Amino acid seqeunce for anti-MSLN antibody of
      CDR2 (VL)

<400> SEQUENCE: 10

Ser Ala Ser Tyr Arg Tyr Pro
1               5

<210> SEQ ID NO 11
<211> LENGTH: 9
<212> TYPE: PRT
<213> ORGANISM: Artificial Sequence
<220> FEATURE:
<223> OTHER INFORMATION: Amino acid seqeunce for anti-MSLN antibody of
      CDR3 (VL)

<400> SEQUENCE: 11

Gln Gln His Tyr Ser Thr Pro Trp Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Amino acid seqeunce for anti-MSLN antibody of
      CDR1 (VH)

<400> SEQUENCE: 12

Gly Tyr Ser Phe Thr Ser Tyr Phe Met His
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Amino acid seqeunce for anti-MSLN antibody of
      CDR1 (VH)

<400> SEQUENCE: 13

Gly Tyr Ser Phe Thr Ser Tyr Phe Ile Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Amino acid seqeunce for anti-MSLN antibody of
      CDR1 (VH)

<400> SEQUENCE: 14

Gly Tyr Ser Phe Thr Ser Tyr Phe Ile Gln
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Amino acid seqeunce for anti-MSLN antibody of

```
        CDR2 (VH)

<400> SEQUENCE: 15

Trp Ile Phe Pro Gly Asn Gly Asn Thr Lys Tyr Ser Gln Lys Phe Gln
1               5                   10                  15
Gly

<210> SEQ ID NO 16
<211> LENGTH: 17
<212> TYPE: PRT
<213> ORGANISM: Artificial Sequence
<220> FEATURE:
<223> OTHER INFORMATION: Amino acid seqeunce for anti-MSLN antibody of
      CDR2 (VH)

<400> SEQUENCE: 16

Gly Ile Phe Pro Gly Ser Gly Asn Ala Asn Tyr Ala Gln Lys Phe Gln
1               5                   10                  15
Gly

<210> SEQ ID NO 17
<211> LENGTH: 17
<212> TYPE: PRT
<213> ORGANISM: Artificial Sequence
<220> FEATURE:
<223> OTHER INFORMATION: Amino acid seqeunce for anti-MSLN antibody of
      CDR2 (VH)

<400> SEQUENCE: 17

Trp Ile Phe Pro Gly Ser Gly Asn Thr Lys Tyr Ser Gln Lys Phe Gln
1               5                   10                  15
Gly

<210> SEQ ID NO 18
<211> LENGTH: 10
<212> TYPE: PRT
<213> ORGANISM: Artificial Sequence
<220> FEATURE:
<223> OTHER INFORMATION: Amino acid seqeunce for anti-MSLN antibody of
      CDR3 (VH)

<400> SEQUENCE: 18

Ser Gly Gly Tyr Gln Tyr Tyr Phe Asp Tyr
1               5                   10
```